US010531877B2

(12) United States Patent
Shabaz et al.

(10) Patent No.: US 10,531,877 B2
(45) Date of Patent: Jan. 14, 2020

(54) INTERLOCKING LOOP COUPLING/DECOUPLING SYSTEM FOR DEPLOYING VASCULAR IMPLANT DEVICES

(71) Applicant: Inceptus Medical LLC, Aliso Viejo, CA (US)

(72) Inventors: Martin Shabaz, Aliso Viejo, CA (US); Claudio Plaza, Irvein, CA (US); Richard Quick, Mission Viejo, CA (US); Paul Lubock, Monarch Beach, CA (US); Brian J. Cox, Laguna Niguel, CA (US)

(73) Assignee: INCEPTUS MEDICAL LLC, Aliso Viejo, CA (US)

( * ) Notice: Subject to any disclaimer, the term of this patent is extended or adjusted under 35 U.S.C. 154(b) by 0 days.

(21) Appl. No.: 16/186,360

(22) Filed: Nov. 9, 2018

(65) Prior Publication Data
US 2019/0133600 A1    May 9, 2019

Related U.S. Application Data

(60) Provisional application No. 62/584,047, filed on Nov. 9, 2017.

(51) Int. Cl.
*A61B 17/12* (2006.01)
*A61B 17/00* (2006.01)

(52) U.S. Cl.
CPC .......... *A61B 17/12109* (2013.01); *A61B 2017/00367* (2013.01); *A61B 2017/00477* (2013.01);
(Continued)

(58) Field of Classification Search
CPC ........ A61B 17/12109; A61B 17/12022; A61B 2017/1205; A61B 2017/12054;
(Continued)

(56) References Cited

U.S. PATENT DOCUMENTS 5,250,071 A * 10/1993 Palermo ................. A45D 42/24
128/898
5,391,172 A   2/1995 Williams et al.
(Continued)

FOREIGN PATENT DOCUMENTS

EP   2218403   8/2010
EP   3064154   9/2016
(Continued)

OTHER PUBLICATIONS

International Search Report on corresponding PCT application (PCT/US2018/060184) from International Searching Authority (KIPO) dated Mar. 4, 2019.
(Continued)

*Primary Examiner* — Diane D Yabut
(74) *Attorney, Agent, or Firm* — Klein, O'Neill & Singh, LLP

(57) ABSTRACT

In a system and method for deployment of an implant device, the implant device includes a first loop at its proximal end, and a deployment tool has a second loop attached at its distal end. A release wire slidably disposed within the deployment tool has a distal end extending through the first and second loops to releasably couple the implant device to the deployment tool, and a proximal portion extending from a proximal end of the deployment tool, which is held in a retraction device. The retraction device is operable to hold the proximal end of the deployment tool and to pull the release wire proximally through the deployment tool until the distal end of the release wire is withdrawn from the first
(Continued)

and second loops to decouple the implant device from the deployment tool.

5 Claims, 8 Drawing Sheets

(52) U.S. Cl.
CPC ............... *A61B 2017/00526* (2013.01); *A61B 2017/00575* (2013.01); *A61B 2017/00592* (2013.01); *A61B 2017/00623* (2013.01); *A61B 2017/12054* (2013.01)

(58) Field of Classification Search
CPC .......... A61B 2017/12113; A61M 2025/09116; B25B 25/00
See application file for complete search history.

(56) References Cited

U.S. PATENT DOCUMENTS

| | | | |
|---|---|---|---|
| 5,601,568 | A | 2/1997 | Chevillon et al. |
| 5,868,755 | A | 2/1999 | Kanner et al. |
| 6,039,744 | A | 3/2000 | Forber |
| 6,146,415 | A | 11/2000 | Fitz |
| 6,338,736 | B1 | 1/2002 | Boosfeld et al. |
| 6,599,296 | B1 | 7/2003 | Gillick et al. |
| 7,371,251 | B2 | 5/2008 | Mitelberg et al. |
| 7,635,382 | B2 | 12/2009 | Pryor |
| 7,674,282 | B2 | 3/2010 | Wu et al. |
| 7,708,754 | B2 | 5/2010 | Balgobin et al. |
| 7,799,052 | B2 | 9/2010 | Balgobin et al. |
| 7,819,892 | B2 | 10/2010 | Balgobin et al. |
| 8,002,739 | B2 | 8/2011 | Lee et al. |
| 8,062,325 | B2 | 11/2011 | Mitelberg et al. |
| 8,062,344 | B2 | 11/2011 | Dorn et al. |
| 8,500,789 | B2 | 8/2013 | Wuebbeling et al. |
| 8,777,978 | B2 | 7/2014 | Strauss et al. |
| 8,777,979 | B2 | 7/2014 | Shrivastava et al. |
| 9,155,656 | B2 | 10/2015 | Schaller et al. |
| 9,220,906 | B2 | 12/2015 | Griswold et al. |
| 9,307,996 | B2 | 4/2016 | Johnson et al. |
| 9,307,999 | B2 | 4/2016 | Li et al. |
| 9,375,333 | B1 | 6/2016 | Aboytes et al. |
| 9,597,224 | B2 | 3/2017 | Lowe et al. |
| 9,622,754 | B2 | 4/2017 | Ramzipoor et al. |
| 9,918,718 | B2 | 3/2018 | Lorenzo |
| 2006/0276827 | A1 | 12/2006 | Mitelberg et al. |
| 2008/0306503 | A1 | 12/2008 | Que et al. |
| 2009/0210046 | A1 | 8/2009 | Shumer et al. |
| 2009/0275971 | A1 | 11/2009 | Kelleher et al. |
| 2010/0168756 | A1 | 7/2010 | Dorn et al. |
| 2011/0061660 | A1 | 3/2011 | Cruzada et al. |
| 2011/0295303 | A1 | 12/2011 | Freudenthal |
| 2014/0277084 | A1 | 9/2014 | Mirigian et al. |
| 2014/0277085 | A1 | 9/2014 | Mirigian et al. |
| 2015/0297245 | A1* | 10/2015 | Lam ..................... A61B 17/162 408/127 |
| 2017/0119399 | A1 | 5/2017 | Aguilar et al. |

FOREIGN PATENT DOCUMENTS

| | | |
|---|---|---|
| WO | WO2007053568 | 5/2007 |
| WO | WO2012003317 | 1/2012 |
| WO | 2015131362 | 9/2015 |

OTHER PUBLICATIONS

Written Opinion on corresponding PCT application (PCT/US2018/060184) from International Searching Authority (KIPO) dated Mar. 4, 2019.

* cited by examiner

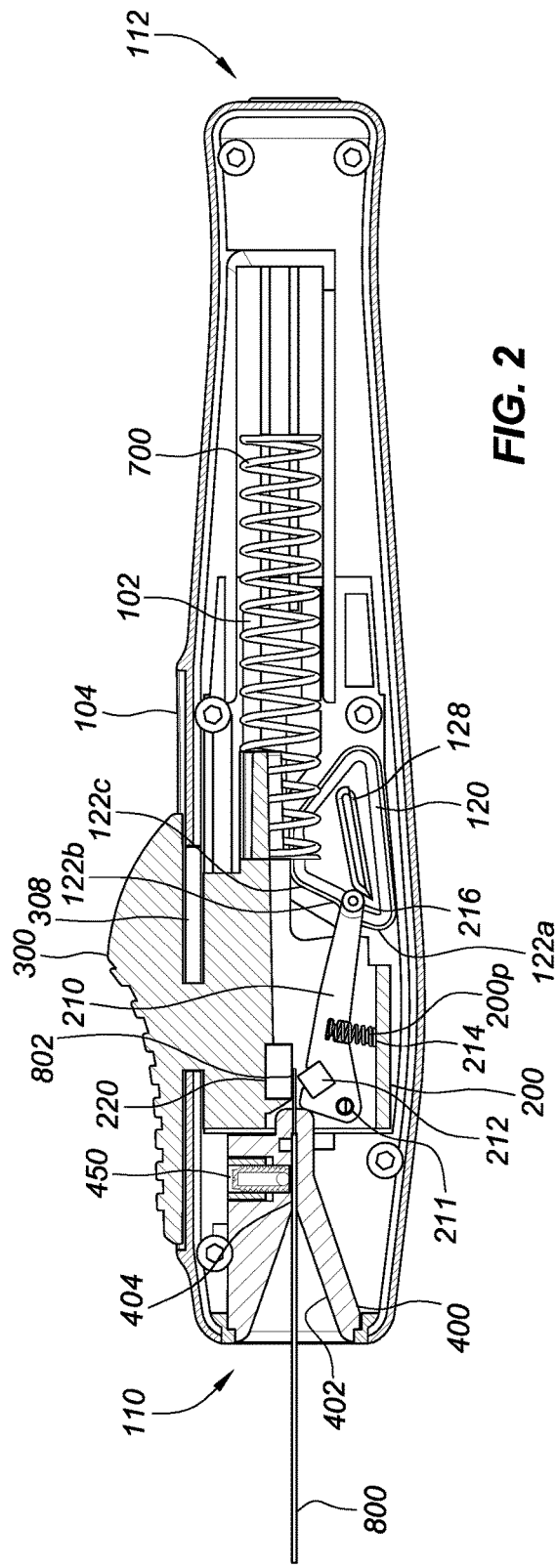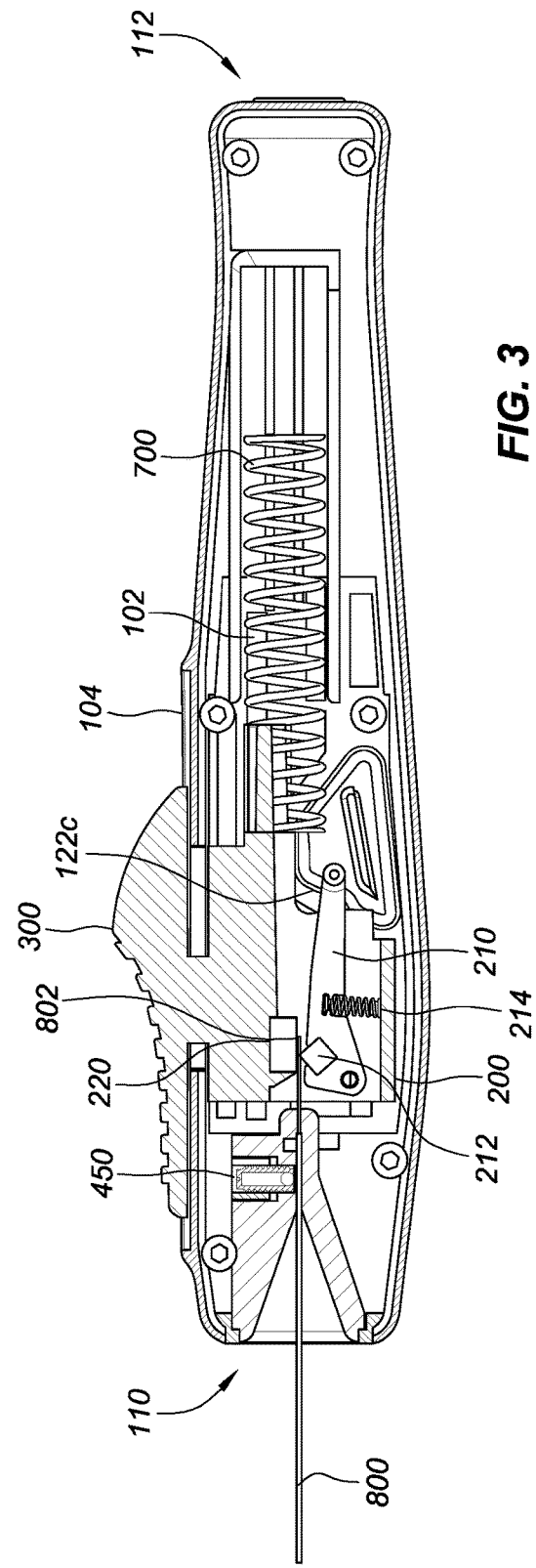

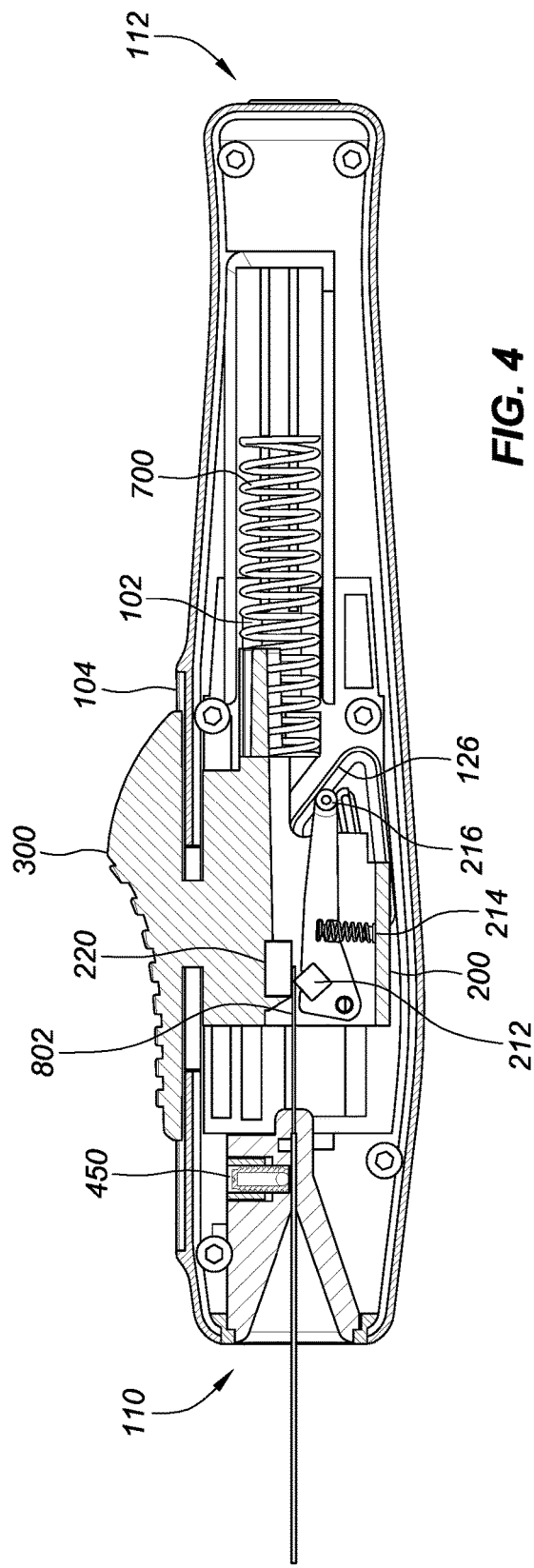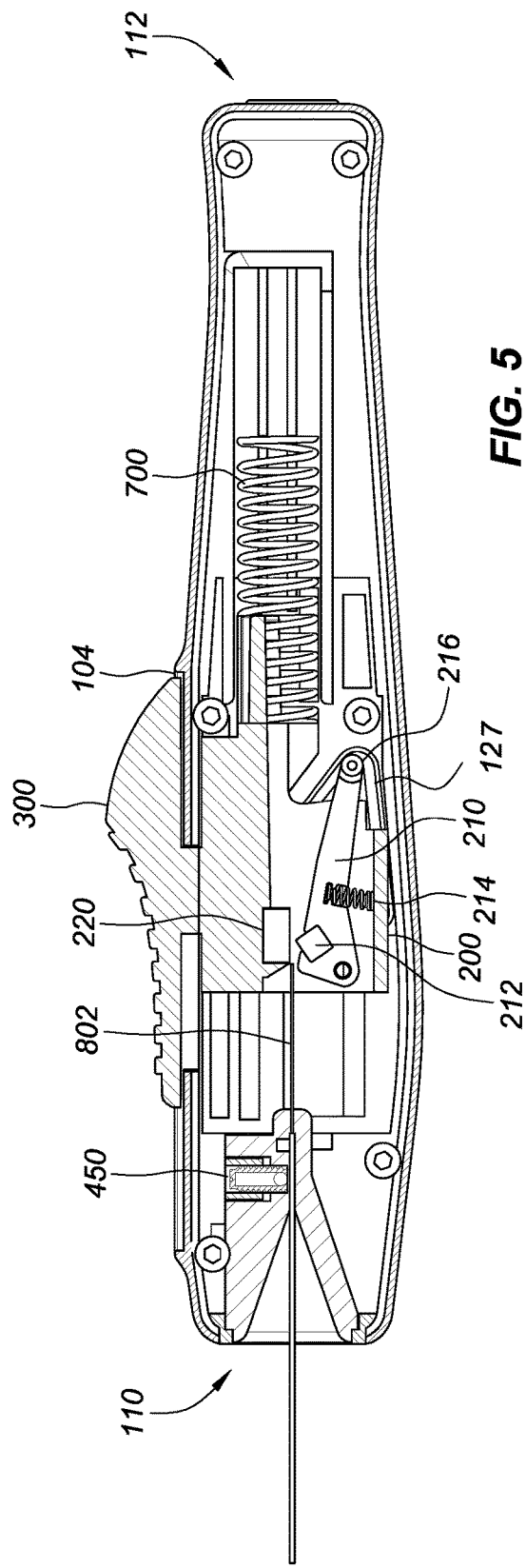

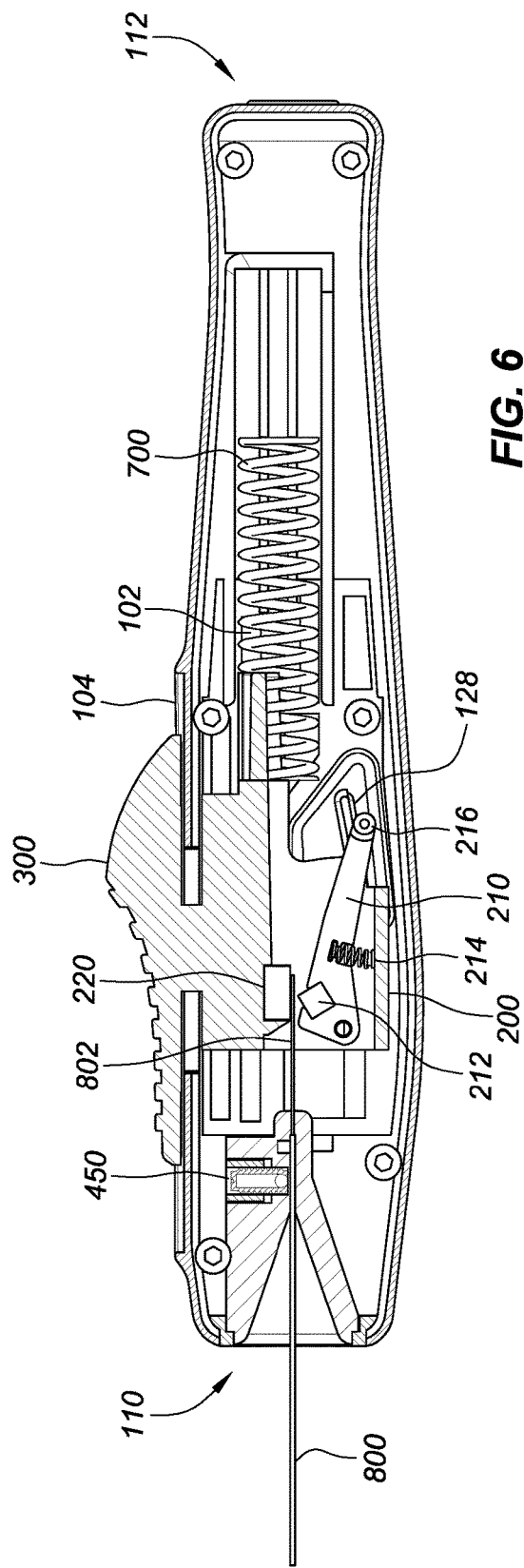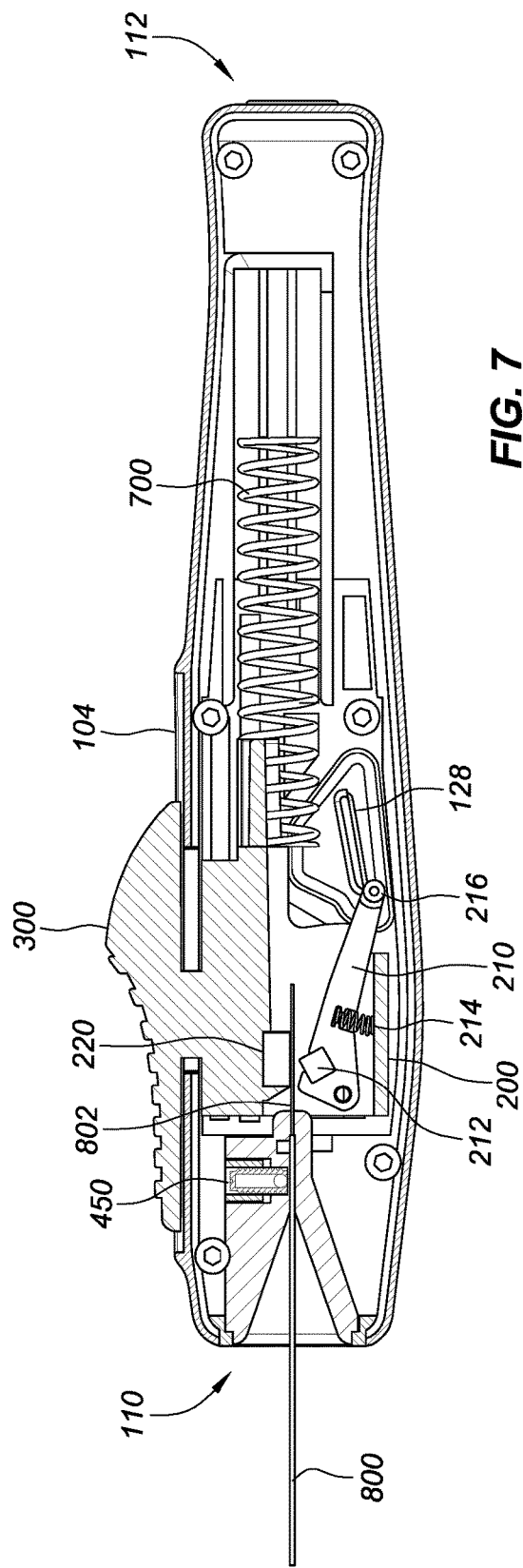
FIG. 6
FIG. 7

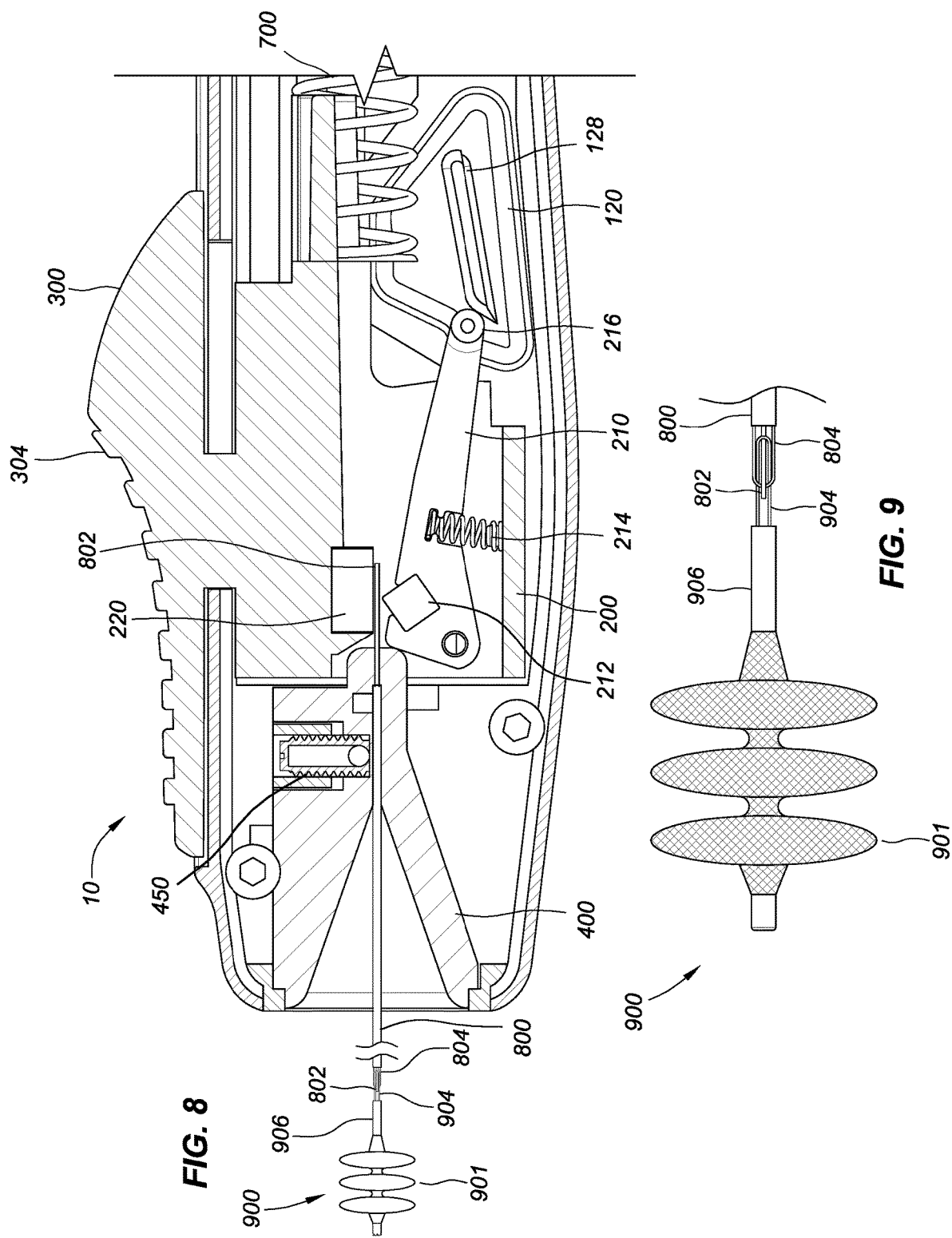

INTERLOCKING LOOP COUPLING/DECOUPLING SYSTEM FOR DEPLOYING VASCULAR IMPLANT DEVICES

CROSS-REFERENCE TO RELATED APPLICATION

This application claims the benefit, under 35 U.S.C. 119(e), of U.S. Provisional Application No. 62/584,047; filed Nov. 9, 2017, the disclosure of which is incorporated herein by reference in its entirety.

FEDERALLY SPONSORED RESEARCH OR DEVELOPMENT

This invention was made with government support under Contract #HHSN268201700015C awarded by NIH/NHLBI (National Institutes of Health/National Heart, Lung, and Blood Institute). The government has certain rights in the invention.

BACKGROUND

The present disclosure pertains to the deployment of vascular implants, such as vascular occlusion devices, and related methods. More specifically, this disclosure relates to systems, devices, and methods for the deployment and release of a vascular implant device at a target vascular site.

In certain implant procedures, such as those used for occlusion of a vascular lumen or other bodily lumen, an implant device is inserted into the body and released at a target site in the lumen. For example, a vascular occlusion implant device can be inserted intravascularly to close or seal blood vessels or close defects in the heart. To insert the implant device, the implant device may advantageously be detachably or releasably coupled to the end of a deployment tool and deployed intravascularly through a delivery device, such as a microcatheter. After placement of the implant device at the target site, the implant device is released or detached from the deployment tool by a suitable release mechanism, and the deployment tool is free to be withdrawn.

It is important that the release or detachment of the implant device be done with the application of minimal axial force to the implant device, so as to minimize the movement of the device from its optimal location at the target vascular site. To this end, release mechanisms have been devised that use, for example, a thermally-fusible link that breaks in response to the application of heat energy through, e.g., electric current. Other release mechanisms use a link that is severed by a shearing or cutting implement. While these mechanisms may achieve, to varying degrees, the object of minimizing the transmission of axial forces to the implant device, they are frequently complex and costly to manufacture, and/or cumbersome to use.

Furthermore, conventional intravascular implant deployment tools require engagement of a release wire through all phases of movement needed for decoupling the implant from the deployment tool. However, this means that in addition to the release wire being retracted by actuation of the deployment tool, the release wire can also be pushed by the deployment tool.

Accordingly, it is still a goal in the relevant arts to provide an implant device release/detachment mechanism that is simple to manufacture and easy to use, while still meeting the necessary clinical criteria.

SUMMARY

The present disclosure relates to embodiments of a system for decoupling a deployed implant device from a deployment tool to which the implant device is coupled during deployment, wherein the deployment tool with the implant device attached to its distal end is passed through an intravascular microcatheter to a vascular target site. The disclosed embodiments include a retraction device to engage and withdraw a release wire having a distal end that detachably couples the implant device to the deployment tool, and a system for detachably coupling the implant device to the distal end of the deployment tool. Specific embodiments of the disclosed detachment system use interlocking loops for coupling the implant device to the deployment tool.

In an aspect, this disclosure relates to an interlocking loop coupling/decoupling system configured to allow a user to detach or release a vascular implant device from a deployment tool through a single action on the retraction device. More specifically, the system disclosed herein includes an interlocking loop coupling mechanism for detachably coupling an implant device to a deployment tool by means of a release wire, and a release wire retraction device that retracts the release wire so as to decouple the implant device from the deployment tool without imparting any significant axial force to the implant device.

The single action retraction device of the present disclosure can avoid reinsertion of the release wire, as the retraction device does not act on the release wire in all phases of movement. Instead, the retraction device only acts on the release wire during retraction of the release wire, and it allows for resetting of the retraction device for use with another deployment tool and implant device. The systems and methods described herein are particularly useful for the endovascular deployment of vascular occlusion implants, but they may also be useful for deployment of stents, coils, plugs and other implant devices for therapeutic or diagnostic benefit of a patient.

In one aspect, a system for deployment of a vascular implant in accordance with this disclosure comprises an implant assembly having a proximal end and a distal end, with a first loop attached to the proximal end of the implant assembly; a deployment tool having a proximal end and a distal end, with a second loop attached to the distal end of the deployment tool; a release wire slidably disposed within the deployment tool and having a proximal end and a distal end, the distal end of the release wire extending through the first and second loops to releasably couple the implant assembly to the deployment tool, the proximal end of the release wire extending proximally from the proximal end of the deployment tool; and a release wire retraction device operable to (a) hold the proximal end of the deployment tool, (b) releasably grip the proximal end of the release wire, and (c) pull the release wire proximally through the deployment tool until the distal end of the release wire is withdrawn from the first and second loops to decouple the implant assembly from the deployment tool.

In another aspect, a method of coupling an implant device to a deployment tool and decoupling the implant device therefrom are disclosed.

BRIEF DESCRIPTION OF THE DRAWINGS

FIG. 2 shows a partial cross sectional view of the retraction device in a first, un-clamped, non-actuated state.

FIG. 3 shows a partial cross sectional view of the retraction device in a second, clamped, non-actuated state.

FIG. 4 shows a partial cross sectional view of the retraction device in a third, clamped, actuated state.

FIG. 5 shows a partial cross sectional view of the retraction device in a fourth, un-clamped, actuated state.

FIG. 6 shows a partial cross sectional view of the retraction device in a fifth, resetting state.

FIG. 7 shows a partial cross sectional view of the retraction device in a sixth, resetting state.

FIG. 8 shows a partial cross sectional view of the interlocking loop coupling/decoupling system as configured prior to actuation to decouple a deployed implant device from a release wire.

FIG. 9 shows a side view of the implant device and the distal end of the interlocking loop coupling system of FIG. 8.

DETAILED DESCRIPTION

Figure 1:
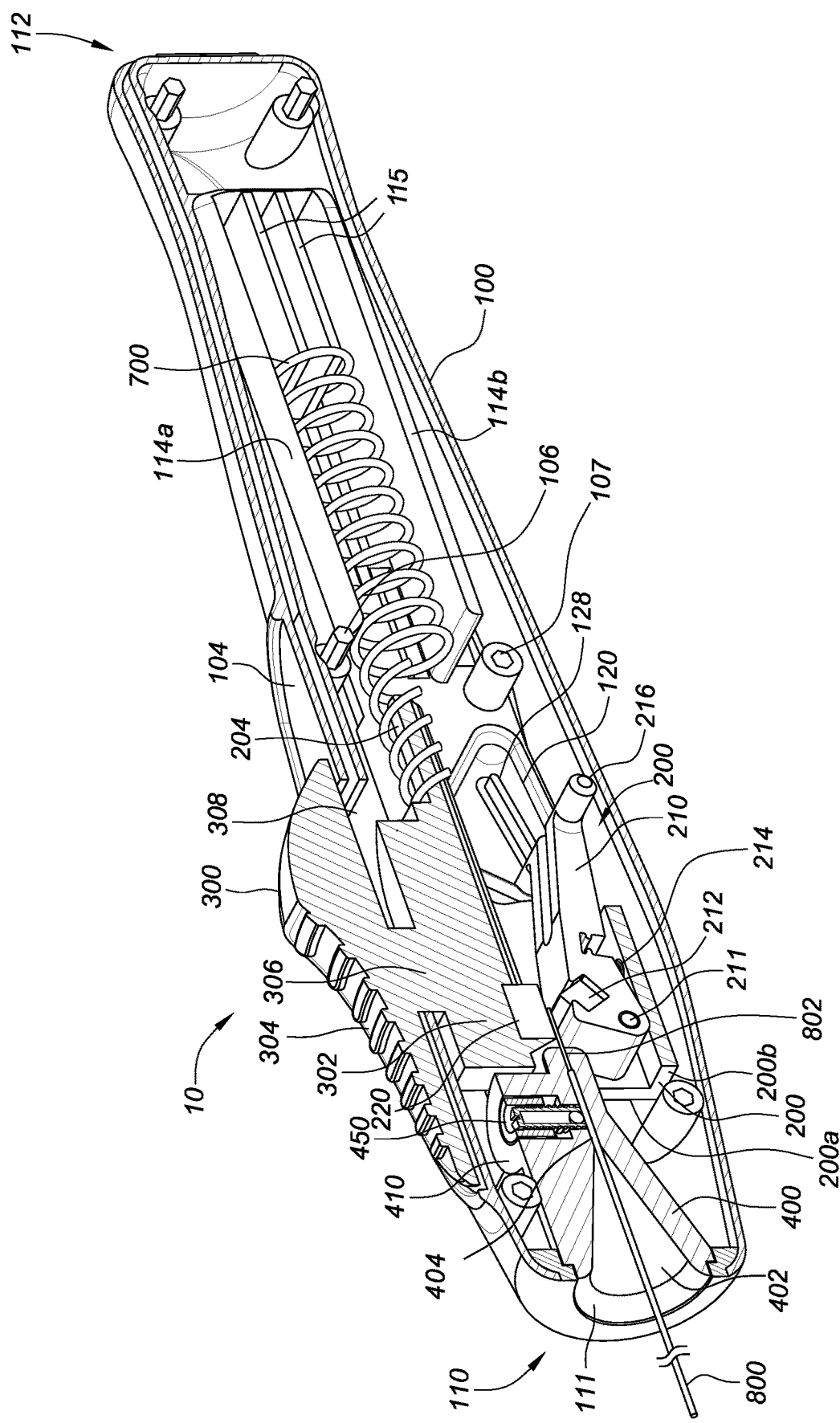
FIG. 1 shows a perspective view with a partial cutaway of a release wire retraction device for use with an interlocking loop implant coupling system in accordance with an aspect of this disclosure.

The detailed description set forth below in connection with the appended drawings is intended as a description of the presently preferred embodiments of an interlocking loop implant coupling/decoupling system with a release wire retraction device provided in accordance with aspects of the present disclosure. It is not intended to represent the only forms in which the presently-disclosed components, assemblies, and methods may be constructed or used. The description sets forth the features and the steps for constructing and using the embodiments of the presently-disclosed components, assemblies, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

FIGS. 1-7 illustrate a partial cutaway of an exemplary embodiment of a retraction device 10 for an interlocking loop implant coupling/decoupling system in accordance with this disclosure. The figures show half of a housing 100 and cross sectional views of a guide assembly 200, an actuator 300, and a release wire guide 400. In some embodiments, the guide assembly 200 and the actuator 300 may be integrally formed as a unit. Alternatively, the guide assembly 200 and the actuator 300 may be separate, mechanically connected components. The guide assembly 200 and the actuator 300 can be understood as being symmetrical along an axis extending from a distal or front end 110 to a proximal or rear end 112 of the retraction device 10. (The terms "distal" and "proximal," as used in this disclosure, are taken from the perspective of the user of the device 10.) Accordingly, the other halves (not shown) of the guide assembly 200 and the actuator 300 can be understood as being reflective of the halves shown in FIGS. 1-7. For ease of assembly, the housing 100 may advantageously be made of two axial halves that are joined together after installation of the interior components by adhesive or other suitable bonding/welding means. For this purpose, each housing half may have complementary male locating pins 106 and female locating sockets 107. A suitable durable plastic or polymeric material is preferred for the housing, although it may also be made of a suitable metal or alloy. Embodiments of the retraction device 10 can be made with components formed by manufacturing processes such as injection molding or machining. Alternatively, formation processes such as 3D printing can also be used. The housing 100, when fully assembled, should advantageously be externally dimensioned and configured as a handpiece that can be comfortably and securely held and manipulated when the device is used.

The housing 100 of the retraction device 10 contains the guide assembly 200, an interior body 302 of the actuator 300, and the release wire guide 400. The actuator 300 and the guide assembly 200 are moveable axially relative to the housing 100 between a distal position and a proximal position by manipulation of a finger grip 304 on the exterior of the housing 100. Specifically, the interior body 302 of the actuator 300 is connected to the finger grip 304 by a connection portion or stem 306 that extends through a longitudinal slot 308 in the top of the housing 100. The guide assembly 200, in turn, is connected to the interior body 302 of the actuator 300 so as to be moveable therewith. The top of the housing 100 is provided with a planar track surface 104 on which the finger grip 304 is slidably seated. The slot 308 and the track surface 104 are configured to define a path for longitudinal movement of the guide assembly 200 and the actuator 300 relative to the housing 100. The guide assembly 200 may comprise side walls 200a, a bottom wall or base 200b, and a top wall 302, which together generally define a central space for the operational components of the guide assembly 200, as will be described below.

In embodiments of the retraction device 10, the guide assembly 200 may include a guide groove or track 120 providing a guide path around a camming ramp 128, a guide lever 210, and a fixed release wire gripping element 220, which may be termed an "anvil." (It is understood that a corresponding guide track 120 is provided in the unshown other half of the housing 100.) The anvil 220 may be attached to at least one of the side walls 200a and the top wall 302 of the guide assembly 200. The anvil 220 can be aluminum or a similar metal, or it can be a durable polymeric or composite material. The guide lever 210 can be rotatably pinned to at least one of the side walls 200a of the guide assembly 200 with a hinge pin 211 near its distal end. The guide lever 210 can further comprise a movable gripping element 212, which be provided as an insert in the guide lever located near the distal end of the guide lever 210 and configured so that the movable gripping element 212 may move toward and away from the anvil 220 as the guide lever 210 pivots (as described below), whereby the proximal end of a release wire 802 extending from the end of a deployment tool sheath 800 inserted into the distal end 110 of the housing 100 can be gripped between the movable gripping element 212 and the anvil 220. The movable gripping element 212 can be an insert in the guide lever 210, as shown, or it may be integral therewith. It may have any suitable shape for providing a secure but releasable engagement with the guide wire against the fixed gripping element or anvil 220.

The guide lever 210 has a free proximal end terminating in a pair of guide arms 216 (only one of which is illustrated), each of which is seated in the guide track 120 in the corresponding housing half. The guide lever 210 is upwardly biased by a guide lever biasing spring 214 (FIGS. 2-7), and it is guided for movement along a continuous closed path provided by the guide tracks 120 within which the arms 216 are seated to move as the actuator 300 and the guide assembly 200 are moved to their different positions, as described below with reference to FIGS. 2-7.

As best shown in FIG. 1, the guide assembly 200 can further include a spring support 204 extending proximally from the top wall 302. An axially-oriented forward biasing spring 700 can be arranged to have a first end encircle the spring support 204 and abut a spring seat formed by the juncture of the spring support 204 and the top wall 302. The forward biasing spring 700 extends proximally through a spring chamber defined between an upper chamber wall 114a and a lower chamber wall 114b, and it terminates in a second end seated on a proximal spring seat 115. In this way, the forward biasing spring 700 provides a distally-directed biasing force against the guide assembly 200, thereby biasing the guide assembly 200 against moving rearward (i.e., proximally) in the housing 100.

The distal end 110 of the housing 100 includes a distal opening 111 through which the deployment tool 800 containing a release wire 802 may enter the release wire guide 400 of the retraction device 10. The deployment tool 800 may be, in embodiments of the disclosure, a sheath through which the release wire 802 is axially and slidably disposed. (For the purposes of this discussion, the deployment tool will be referred to as a "sheath," although other configurations for deployment tool may be used.) The release wire guide 400 may advantageously have a cone-shaped entry 402 tapering inwardly and proximally to an axial passage 404. This tapering shape allows the sheath 800 with the release wire 802 to be inserted by a user while then being positioned for insertion through the guide assembly 200. The sheath 800 may advantageously be retained within the passage 404 by a sheath retention device 450, such as a ball-nosed spring plunger or other similar retention element or mechanism housed in a proximal portion 410 of the release wire guide 400, that provides a radial retention force against the sheath 800, whereby the proximal end of the sheath 800 is held in a fixed position as the release wire 802 is pulled proximally through it by the retraction device 10, as described below. In some embodiments, the sheath retention device 450 can be an integral unit, such as a spring plunger of the type marketed by Vlier Products (www.vlier.com). In other embodiments, the sheath retention device 450 can comprise separate components, such as a ball bearing, a spring, and a set screw. The release wire guide 400 can be a separate component from the housing 100, or it can be integrally molded with the housing 100. The sheath retention device 450 can be attached to the release wire guide 400 by a threaded connection or by alternative means, such as adhesive, fasteners, or other suitable ways.

FIGS. 2-7 illustrate partial cross sectional views of the retraction device 10 at various stages in an actuation cycle for proximal movement of the release wire in a linear fashion by manual manipulation of the actuator 300. The operation described below is defined in a sequence of steps or stages, each of which corresponds to a position of the actuator 300 and the guide assembly 200, particularly the positions of the guide arms 216 in the guide track 120. The path defined by the guide track 120 that is followed by the guide arms 216 defines a closed loop shape that may be, for example, generally ovoid, oblong, trapezoidal, rhomboidal, rectangular, or triangular. In the illustrated exemplary embodiment, the guide track 120 has a generally trapezoidal shape. In operation, the movable gripping element 212 can be disengaged from the release wire 802 at a most distal position and at a most proximal position of the path. The movable gripping element 212 can be engaged with the release wire 802 at intermediate positions of the path between the most distal position and the most proximal position.

FIG. 2 illustrates the retraction device 10 in a first, non-actuated stage that is considered an "at-rest position." In this first stage, the guide arms 216 are positioned at a first or starting position 122b in the guide track 120, wherein the starting position 122b is between a lower distal portion 122a and an upper distal portion 122c of the guide track 120. In this first stage, the actuator 300 is in a forward (distal) position, and the forward biasing spring 700 is biasing the guide assembly 200 forward (distally). Additionally, the guide lever biasing spring 214 is biasing the guide lever 210 upward towards the actuator 300. The combined forces of the forward biasing spring 700 and the guide lever biasing spring 214 results in the guide arms 216 contacting and stopping at the starting position 122b in the guide track 120. At this point, in some embodiments, the guide lever 210 is positioned so that the movable gripping element 212 does not contact a proximal portion of the release wire 802 that is extending proximally out of the sheath 800.

FIG. 3 illustrates the retraction device in a second, clamped, but non-actuated stage, in which the actuator 300 is moved rearwardly (proximally) by a user to a first intermediate position along the top track surface 104. In this position, the guide assembly 200 has moved rearwardly (proximally), such that the guide arms 216 are shifted away from the starting position 122b of the guide track 120, thereby allowing the guide lever biasing spring 214 to urge the proximal end of the guide lever 210 upward as the guide arms 216 track toward upper distal portion 122c of the guide track 120. In this state, the rearward movement of the actuator 300 and the guide assembly 200 compresses the forward biasing spring 700. As the guide lever 210 is urged upward, the release wire 802 is gripped between the movable gripping element 212 and the anvil 220, and the release wire 802 begins to be retracted rearwardly (proximally) into the housing 100 proportionately as the guide assembly 200 is moved proximally with the actuator 300.

FIG. 4 illustrates the retraction device in a third, actuated stage, in which the actuator 300 is further moved rearwardly (proximally) by a user to a second intermediate position along the top track surface 104, rearward (proximal) from the first intermediate position shown in FIG. 3. In this position, the guide assembly 200 has moved rearwardly (proximally), such that the guide arms 216 are now positioned at a first or upper proximal portion 126 of the guide track 120 and at a proximal end of the camming ramp 128. In the illustrated exemplary embodiment, in which the guide track 120 has a generally trapezoidal shape, rearward movement of the guide lever 210 results in the guide arms 216 being positioned at the first proximal portion 126 of the guide track 120, while the distal end of the guide lever 210 (in which the gripping movable gripping element 212 is located) is moved away from the release wire 802. Due to the slope of the proximal portion of the guide track 120, the guide lever 210 is urged downward, against the biasing force of the guide lever biasing spring 214, thereby removing the gripping insert 212 from its engagement with the release wire 802, and thus halting the proximal movement of the release wire 802 into the housing 100. The distance that the release wire 802 is advanced proximally into the housing between the second and third stages (FIGS. 3 and 4, respectively) before being halted is determined largely by the length of the path travelled by the guide arms 216 in the guide track 120 from the second distal portion 122c to the first proximal portion 126 thereof.

FIG. 5 illustrates the retraction device in a fourth, actuated stage, in which the actuator 300 is at a rearmost (proximal) position along the top track surface 104. In this position, the guide assembly 200 has moved rearwardly such that the guide arms 216 pass over the proximal end of the camming ramp 128 to a second or lower proximal portion 127 of the guide track 120, where by the actuator 300 and the guide assembly have reached their proximal limit of travel against the biasing force of the forward biasing spring 700. Similarly, the guide lever 210 has moved downwardly into a lower portion of its range of travel against the biasing force of the guide lever biasing spring 214, thereby moving the movable gripping element 212 further away from (and out of engagement with) the release wire 802.

Figure 12:
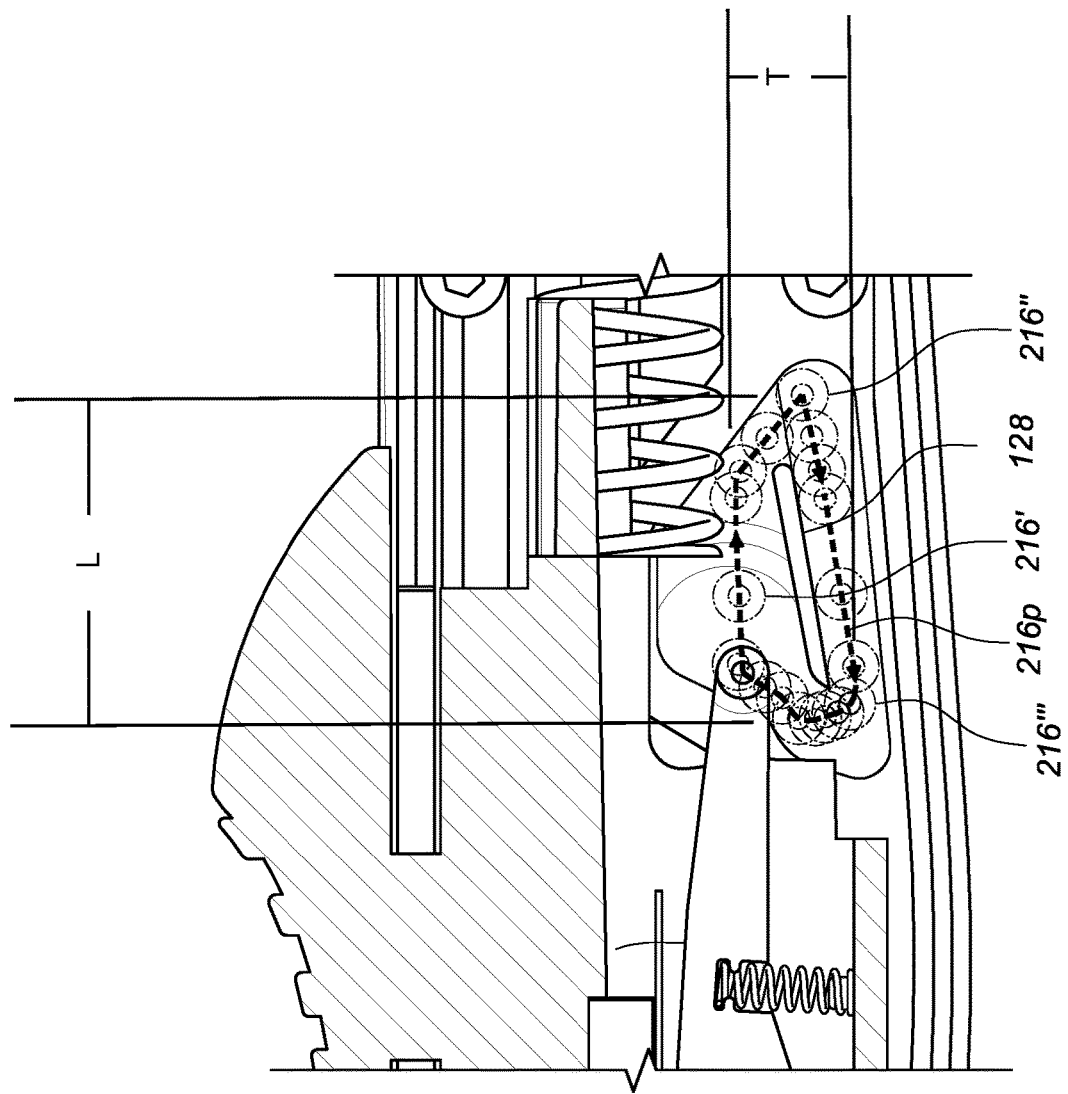
FIG. 12 shows an exemplary guide track for the guide arms around a camming ramp of the retraction device of FIGS. 1-7.

The guide arms 216 may move in a closed path where the longitudinal (parallel to the axis of movement of the sheath 800 and release wire 802) distance L is greater than the transverse distance T, as shown in FIG. 12. In some embodiments, the ratio of the longitudinal distance to the transverse distance (L/T) is at least 1.25 and may be between approximately 1.5 and 15. In some embodiments, the path may define a closed shape with between about 3 and 6 substantially linear sides. An exemplary closed loop movement path 216p of the guide arms 216 around the camming ramp 128 is indicated in FIG. 12 by a broken line showing various positions 216', 216", and 216" in the movement path.

FIGS. 6 and 7 illustrate the retraction device in a fifth, resetting stage, in which the actuator 300 and the guide assembly 200 travel forward towards the distal end 110 of the retraction device 10. When the finger grip 304 of the actuator 300 is released, the forward biasing spring 700 urges the actuator 300 and the guide assembly in the distal direction. Due to the geometry of the guide track 120, the guide arms 216 follow a movement path below the camming ramp 128, in contrast to the actuation stages (i.e., the third and fourth stages shown in FIGS. 4 and 5, respectively) in which the guide arms 216 follow a movement path above the camming ramp 128. As the guide arms 216 move distally in the portion of the guide track 120 below the camming ramp 120, the proximal end of the guide lever 210 is rotated downwardly (clockwise as shown in the drawings) against the upward biasing force of the guide lever biasing spring 214, which is further compressed. The clockwise rotation of the guide lever 210 moves the movable gripping element 212 further away from the release wire, so that the axial position of the release wire 802 within the housing 100 is not changed or affected as the actuator 300 and the guide assembly 200 are moved distally by the forward biasing spring 700 back to the first stage illustrated in FIG. 2.

FIG. 7 shows the actuator 300 and the guide assembly 200 having been moved back distally nearly to the position shown in FIG. 2, closer to the distal end 110 of the retraction device 10 than is shown in FIG. 6. The guide arms 216 continue to follow a movement path below the camming ramp 128, until they reach a distal edge of the camming ramp 128. In the movement path of the guide arms 216 below the camming ramp 128, the guide lever 210 is maintained in the lower portion of its range of travel shown in FIG. 6, with the movable gripping element 212 maintaining its disengagement from the release wire 802. Further movement of the guide arms 216 distally in the guide track 120 results in the guide arms 216 clearing the distal end of the camming ramp 128. As the guide arms 216 enter the first distal portion 122a of the guide track 120, the guide lever biasing spring 214 biases the guide lever 210 back to the first or starting position 122b in the guide track as shown in FIG. 2, wherein gripping element 212 is not contacting the release wire 802. At this point, the retraction device is reset back to the first or at-rest stage shown in FIG. 2. During or after the resetting of the retraction device (i.e., once the movable gripping element releases the guide wire 802), the retraction device 10 may be separated from the sheath 800 and the guide wire 802, thereby allowing the retraction device 10, once reset, to be used in another implant device decoupling application.

In summary, FIGS. 2-7 illustrate a sequence of operational steps or stages of the retraction device 10, in which the retraction device 10 is operable to retract or withdraw the release wire 802 from an implant deployed at a target vascular site, whereby the withdrawal is accomplished uni-directionally (i.e., proximally), without disturbing or moving implant or subjecting the implant or the deployment tool to any significant axial force.

Different geometries for the guide track 120 and the camming element 128 can be provided. In the illustrated exemplary embodiment, a generally trapezoidal shape for the guide track 120 is provided, with a ramp-like camming element 128. However, alternative guide track and camming element geometries can be used to achieve the result of retracting the release wire during actuation, while allowing the guide assembly to be reset without reversing the direction of movement of the release wire 802 (i.e., without advancing the release wire 802).

The fulcrum point (i.e., the pin 211) of the guide lever 210, and/or the shape of the guide lever 210, can be defined such that the movement of the guide arms 216 is different from that of the embodiment shown in FIGS. 2-7. For example, an embodiment may be provided in which the fixed gripping element ("anvil") 220 and the movable gripping element 212 act on the release wire 802 when the guide arms 216 engage a bottom portion of the guide track 120 instead of the top portion. Moreover, the guiding function provided by the guide track 120 can be provided by a raised wall or rib on the interior surface of the housing 100, along which each of the guide arms 216 travels.

Also, variations for actuator can be achieved through other mechanisms. For example, a uni-directional rotating spool can be used, in which case a rotating dial may be provided for actuation by a user. Such a device may allow for retraction of the release wire by rotation in one direction and slipping in the opposite direction, such as would be understood from a ratcheting socket wrench.

FIGS. 8-11 illustrate the retraction device 10 in combination with an implant assembly 900 releasably coupled to a deployment tool (such as, e.g., the sheath 800) by an interlocking loop coupling system. The implant assembly 900 can include an implant device 901 (e.g., a vascular occluder, as shown), and an implant loop 904 that may be attached to the implant device 901 by a crimp portion 906 at the proximal end of the implant device 901.

FIGS. 8 and 9 illustrate the interlocking loop coupling system in a non-detached state, i.e., when the implant assembly 900 is coupled to the deployment tool (e.g., the sheath 800) during deployment of the implant assembly at a target vascular site. FIG. 8 illustrates the retraction device 10 engaging the proximal portion of a release wire 802 extending proximally from the proximal end of a sheath 800, the distal end of which extends distally from the distal end of the sheath 800, as shown in FIG. 9. Referring still to FIG. 9, a tool loop 804 is attached to the distal end of the sheath 800 containing the release wire 802, whereby the tool loop 804 can be placed through, or overlapped with, the implant loop 904. The distal end or portion of the release wire 802 is extended through the tool loop 804 and the implant loop 904, thereby detachably connecting the loops 804, 904. The placement of the release wire 802 through the loops 804, 904 thus releasably couples the implant assembly 900 to the deployment tool (sheath) 800, preventing their separation. In some embodiments, the crimp portion 906 may have a recess for receiving the distal end of the release wire 802 when the tool loop 804 and the implant loop 904 are coupled together as interlocking loops. Alternatively, the implant loop 904 can be provided inside the tool loop 804, or the implant loop 904 and the tool loop 804 can be assembled in an overlaid fashion without either loop entering the other.

In aspects of the implant assembly 900, the implant loop 904 may be a loop extending only into the crimping portion 906, where the implant loop 904 is fixed to the implant 901 by way of crimping, welding, adhesive, or other suitable methods. In this way, the amount of material necessary for the implant loop 904 can be reduced, and the implant loop 904 can be independently adjusted depending on the implantation technique. Although the exemplary embodiments use a loop, alternative geometries can be used. For example, a braid, cable or wound loop or coil structure within the loop can be provided.

Figure 10:
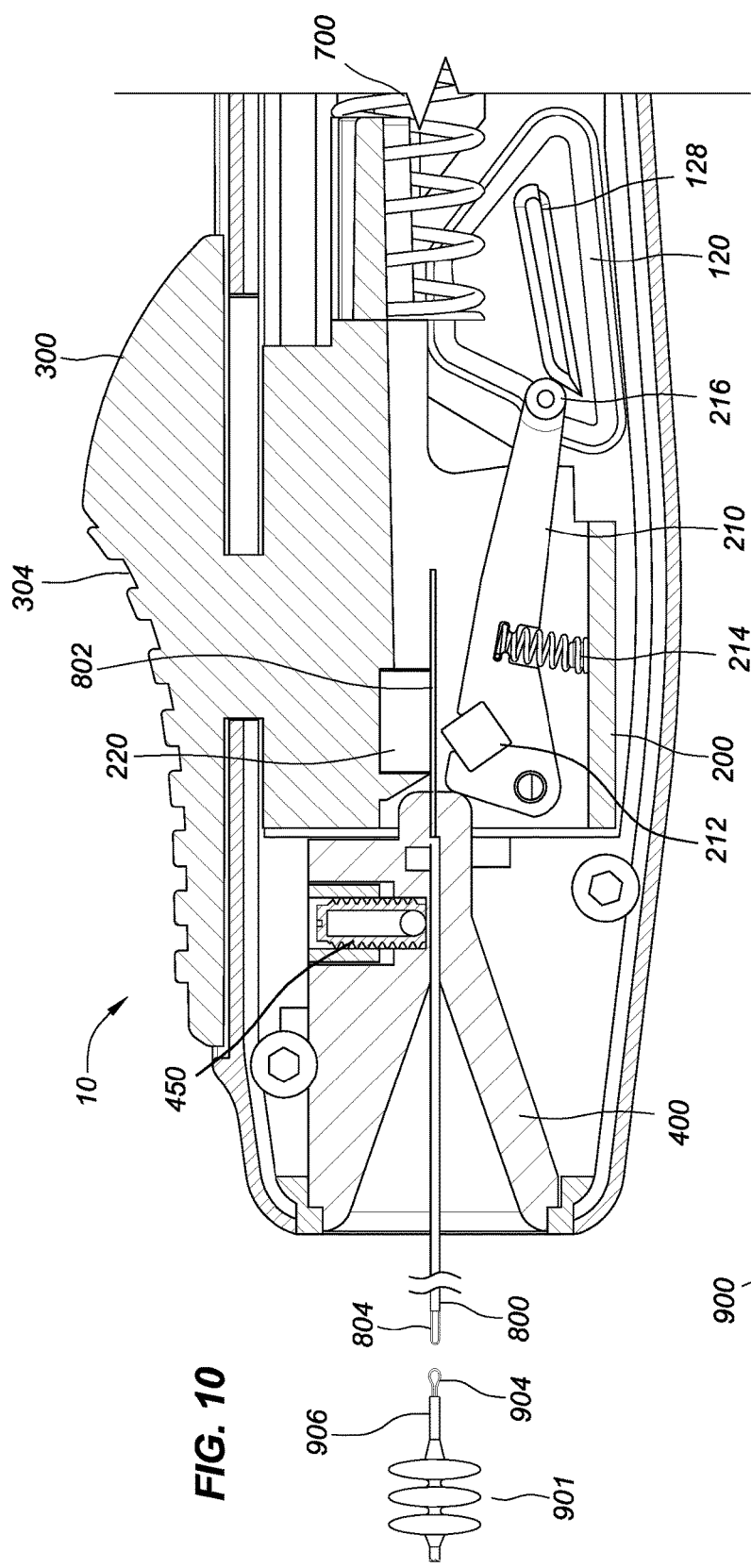
FIG. 10 shows a partial cross sectional view of the interlocking loop coupling system after decoupling.
Figure 11:
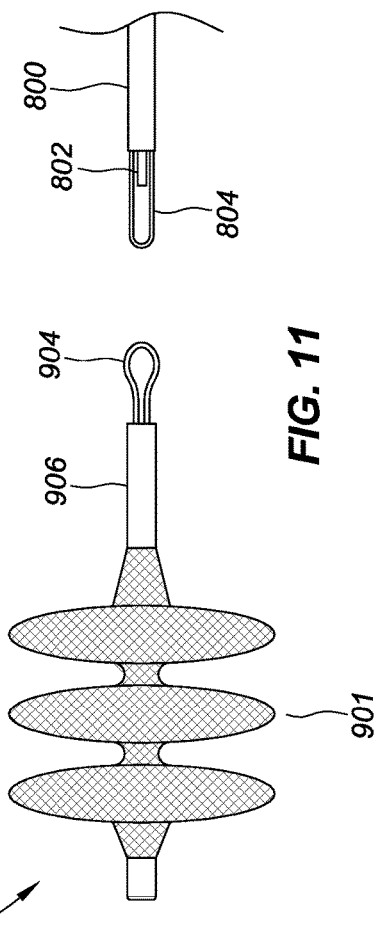
FIG. 11 shows a side view of the implant device and the distal end of the interlocking loop coupling system after decoupling.

FIGS. 10 and 11 illustrate the interlocking loop coupling system in a detached state, i.e., when the implant assembly 900 has been released or decoupled from the sheath 800 after deployment. To detach the implant assembly, the release wire 802 is withdrawn (in the proximal direction) by means such as the retraction device 10 described above, from both the tool loop 804 and the implant loop 904. Thus, the retraction device 10 (or a functional equivalent) is operated to retract the release wire 802, thereby decoupling the implant loop 904 from the tool loop 804. Because the implant loop 904 and the tool loop 804 are not tied together or mechanically connected to each other, they are released from one another solely in response to the retraction of the release wire 802, thereby releasing or decoupling the implant assembly 900 from the sheath 800. The decoupling of the implant assembly is thus accomplished without a significant axial force being applied to the implant once the implant assembly is located and deployed in the target vascular site, thereby minimizing the chance of dislodgement or displacement of the implant from the target site.

Withdrawal of the release wire 802 from engagement with the tool loop 804 and the implant loop 904, resulting in release of the implant, may be detected by a sensor (not shown) inside the retraction device 10 that may indicate to the user confirmation that detachment has occurred. The sensor may detect the proximity or contact with release wire 802 or an element connected to the release wire. The sensor may communicate mechanically or electrically to an indicator element that is in visual or physical contact with the user or visible to the user. For example, a small light or light emitting diode (LED) may be incorporated into the retraction device 10 that is connected to a power source and the sensor so as to indicate movement of release wire 802 sufficient for release of the implant.

Figure 13:
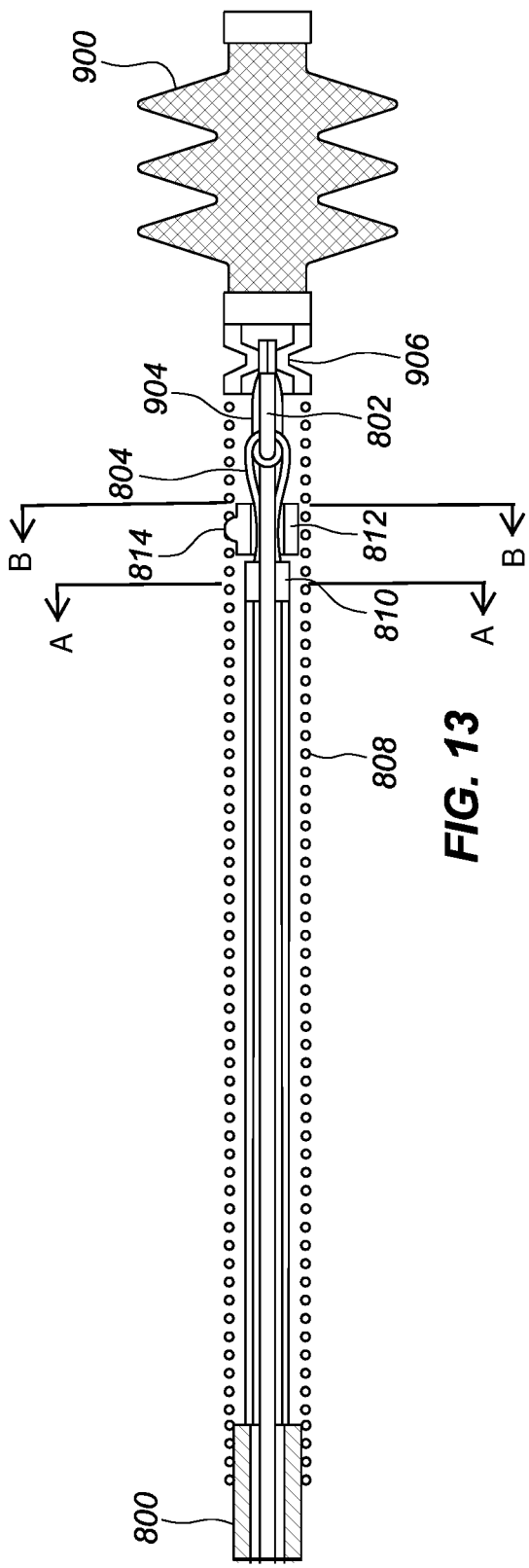
FIG. 13 shows an embodiment of the coupling system with a release wire ferrule and a stop tube.
Figure 15:
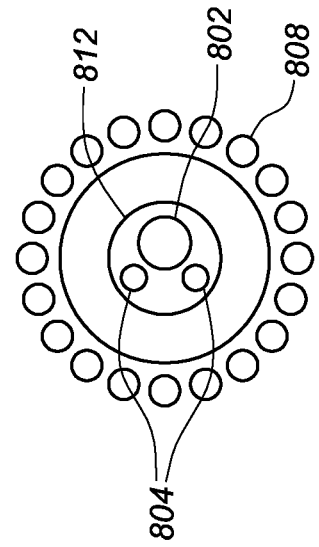
FIG. 15 shows a cross sectional view taken along line B-B of FIG. 13.
Figure 14:
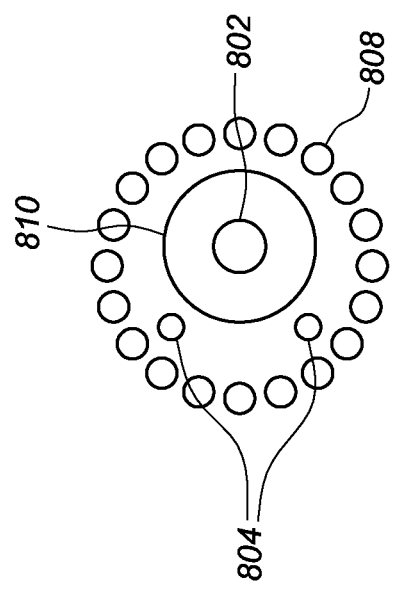
FIG. 14 shows a cross sectional view taken along line A-A of FIG. 13.

In some embodiments, as shown in FIGS. 13-15, an overcoil 808 may extend axially between the distal end of the sheath 800 and the proximal end (e.g., the crimp portion 906) of the implant assembly 900, thereby extending coaxially around the loops 804, 904 and the distal end of the release wire 802 interconnecting them. The overcoil 808 may be either a unifilar or multifilar helical coil made from a metal, a polymer, or a composite. As further shown in FIGS. 13-15, embodiments of the interlocking loop coupling system may include a tubular or annular stop 812 attached to the overcoil 808 proximally from the tool loop 804, and a tubular ferrule 810 attached to the release wire 802 proximally from the stop 812. The ferrule 810 and the stop 812 are configured to reduce the probability of undesirable movement of the release wire 802, as explained below.

It may be advantageous to minimize any tortuous movement of the release wire 802, and to avoid having the release wire 802 extend past a distal end of the overcoil 808. Specifically, it is advantageous to avoid having a loose end of the release wire 802 extend away from the overcoil 808 or the implant assembly 900. Tortuous movement can occur, for example, if the implant assembly 900 encounters high friction in the delivery microcatheter. As friction increases when the user continues to push at the proximal end of the delivery device, the overcoil 808 may start to compress. As the overcoil 808 compresses while the implant position is axially fixed, the distal end of the release wire 802 may potentially extend in an undesired direction. The release wire ferrule 810 and the stop tube 812 help minimize undesirable movement of the release wire 802 during movement of the delivery device and positioning of the implant assembly 900 in the target site. The ferrule 810 and the stop 812 may be made of any suitable metallic or non-metallic material, such as for example, a stainless steel, a polymer, or a composite. The ferrule 810 can be attached to the release wire 802 by any suitable means, such as an adhesive, or by crimping, welding, soldering, or other suitable methods. The ferrule 810 and the stop 812 are internally dimensioned so that the tool loop 804 and the release wire 802 may move freely within the overcoil 808. The stop 812 may be attached to an inner surface of the overcoil 808 at one or more attachment points 814, such as by laser welding, sonic welding, adhesive, or other methods. The stop 812, being distal of the ferrule 810, thereby can act as a stop to limit distal movement of the ferrule 810. As the ferrule 810 is attached the release wire 802, the stop 812 thereby also acts as a stop to limit distal movement of the release wire 802 relative to the loops 804, 904.

The inner diameter of the stop 812 is advantageously sized to allow the tool loop 804 and release wire 802, but not the ferrule 810, to pass through it freely. Thus, even under high friction scenarios, the ferrule 810 is pushed against the stop 812 and prevents any further distal movement of the release wire 802 relative to the overcoil 808. Also, due to the free passage allowed the release wire 802, the stop 812 will not impede movement in the reverse direction, which is required for implant detachment. The ferrule 810 is thus blocked from further advancement distally due to its outer diameter not fitting through the inner diameter of the stop 812.

FIG. 14 is a cross-sectional view taken along line A-A of FIG. 13, showing the arrangement of the ferrule 810 coaxially surrounding the release wire 802. The tool loop 804 may be adjacent to the release wire ferrule 810 inside the overcoil 808. FIG. 15 is a cross-sectional view taken along line B-B of FIG. 13, showing the arrangement of the stop 812 inside the overcoil 808. Both the tool loop 804 and the release wire 802 may be inside the stop 812. That is, the stop 812 coaxially surrounds both the tool loop 804 and the release wire 802.

An implant coupling/decoupling system in accordance with the subject matter of this disclosure may be operated as follows:

A release wire is provided that is slidably disposed within a deployment tool having a proximal end a distal end terminating in a first loop, the release wire having a proximal end that extends proximally a short distance from the proximal end of the deployment tool, and a distal end that passes through the first loop and a second loop at the proximal end of the implant device so as to releasably couple the implant device to the distal end of the deployment tool. The proximal end of the deployment tool is introduced into a distal opening of a release wire retraction device and is fixed within the retraction device with the proximal end of the release wire extending proximally from the proximal end of the deployment tool. The retraction device is operated to (1) grip the proximal end of the release wire, (2) pull the release wire proximally through the deployment tool to withdraw the release wire from the first and second loops, thereby decoupling the implant device from the deployment tool, and (3) disengage from the release wire after proximal movement of the release wire.

In another aspect, the method according to this disclosure may comprise: (1) providing a deployment tool having a first loop attached to its distal end; (2) providing an implant device having a second loop at its proximal end; (3) passing a release wire axially through the deployment tool so that a distal end of the release wire passes through the first and second loops to releasably couple the implant device to the deployment tool, and so that a portion of the release wire is exposed at the proximal end of the deployment tool; (4) gripping the exposed portion of the release wire; and (5) pulling the release wire proximally through the deployment tool until the distal end of the release wire is withdrawn from the first and second loops to decouple the implant device from the deployment tool.

Although exemplary embodiments of the subject matter of this disclosure have been specifically described and illustrated herein, many modifications and variations will be apparent to those skilled in the art. Accordingly, it is to be understood that the retraction device and the interlocking loop coupling system, their respective components, and related methods as disclosed herein may be embodied other than as described herein. It will also be appreciated that the interlocking loop coupling system described above is well-suited for use with the previously-described release wire retraction device. Accordingly, it is contemplated that there will be many applications and situations in which they will be used together in implant device deployment systems and methods in which the implant device is deployed by means of a release wire. In other applications and situations, however, it may be advantageous either to use the interlocking loop coupling system described above with other types of retraction devices, or the above-described retraction device with other types of implant/release wire coupling systems and arrangements.

What is claimed is:

1. A device for retracting a release wire having a distal end releasably coupling a vascular implant device to a distal end of an intravascularly-introduced deployment tool, wherein the deployment tool has a proximal portion from which a proximal portion of the release wire is exposed, the device comprising:
    a housing having a distal opening configured for receiving the proximal portion of the deployment tool from which the proximal portion of the release wire is exposed;
    a gripping assembly in the housing and configured for releasably gripping the exposed proximal portion of the release wire;
    a guide assembly movably mounted in the housing between a distal position and a proximal position, and operatively connected to the gripping assembly to move the gripping assembly between engagement with and disengagement from the exposed proximal portion of the release wire; and
    an actuator having an external portion configured for manipulation distally and proximally by a user, and an internal portion operatively connected to the guide assembly for moving the guide assembly between the distal position and the proximal position;
    wherein the gripping assembly comprises a fixed gripping element fixed in position in the housing, and a movable gripping element operatively connected to the guide assembly to be moved between a position of engagement with the exposed proximal portion of the release wire when the guide assembly is in an intermediate position and a position of disengagement from the exposed proximal portion of the release wire when the guide assembly is in the proximal position; and
    wherein the guide assembly comprises a lever having a first end in which the movable gripping element is disposed, and a second end movably seated in a guide path defined by a track in the guide assembly, wherein the track is configured to move the lever so as bring the movable gripping element into engagement with the exposed proximal portion of the release wire as the guide assembly is moved proximally, and to move the lever to disengage the movable gripping element from the exposed proximal portion of the release wire as the guide assembly is moved distally.

2. The device of claim 1, wherein the guide assembly is operatively connected to the gripping assembly to engage the exposed proximal portion of the release wire when the guide assembly is in an intermediate position, and to disengage from the exposed proximal portion of the release wire when the guide assembly is in the proximal position.

3. The device of claim 1, wherein the guide assembly is spring-biased toward the distal position.

4. The device of claim 1, wherein the track defining the guide path is configured as a closed loop.

5. The device of claim 1, wherein the second end of the lever is configured as a guide arm movably engaged with the track.

* * * * *